United States Patent [19]

Cahill et al.

[11] Patent Number: 5,593,895
[45] Date of Patent: Jan. 14, 1997

[54] METHOD FOR THE DETECTION OF PROTEIN IN URINE

[75] Inventors: Sally E. Cahill, Union, Mich.; Michael J. Pugia, Granger; Robert J. Schaeper, South Bend, both of Ind.

[73] Assignee: Bayer Corporation, Elkhart, Ind.

[21] Appl. No.: 548,437

[22] Filed: Oct. 26, 1995

Related U.S. Application Data

[63] Continuation-in-part of Ser. No. 429,584, Apr. 27, 1995, abandoned.

[51] Int. Cl.$^6$ .................................................. G01N 33/00
[52] U.S. Cl. ............................ 436/86; 436/169; 422/56; 435/287.7
[58] Field of Search ........................ 422/55, 56, 57; 436/86, 88, 169, 170, 810; 435/287.7, 287.8

[56] References Cited

U.S. PATENT DOCUMENTS

| | | | |
|---|---|---|---|
| 3,485,587 | 12/1969 | Keston | 436/86 |
| 4,013,416 | 3/1977 | Rittersdorf et al. | 422/56 |
| 4,333,733 | 6/1982 | Sanford et al. | 436/88 |
| 4,960,710 | 10/1990 | Lau | 436/86 |
| 5,279,790 | 1/1994 | Corey et al. | 422/56 |
| 5,312,591 | 5/1994 | Doi | 422/56 |
| 5,326,707 | 7/1994 | Franke et al. | 436/86 |
| 5,424,215 | 6/1995 | Albarella et al. | 436/86 |

*Primary Examiner*—Jill Warden
*Assistant Examiner*—Maureen M. Wallenhorst
*Attorney, Agent, or Firm*—Jerome L. Jeffers

[57] ABSTRACT

Disclosed is an test for the detection of protein in urine by the use of a reagent system containing a buffer and a protein error indicator. The method involves the use of tartaric acid as cation sensing buffer in combination with a non-cation sensing buffer as the buffer system in order to reduce the incidence of false positive results while using less total buffering material.

13 Claims, No Drawings

METHOD FOR THE DETECTION OF PROTEIN IN URINE

This application is a continuation-in-part of U.S. patent application Ser. No. 08/429,584, filed Apr. 27, 1995.

BACKGROUND OF THE INVENTION

The present invention is related to the detection of protein in urine by the use of a test strip containing a protein error indicator and a buffer. More particularly, it relates to the use of a particular buffer, referred to herein as a "cation sensing buffer" which, when used in combination with typical buffer systems, helps to alleviate the result distorting effects which are observed when high specific gravity (SG) urine is tested for protein content in this manner.

The determination of the presence of protein in a urine sample is important in the diagnosis of several pathological conditions affecting the kidney and circulatory systems as well as the central nervous system. It is often necessary to qualitatively and quantitatively measure protein in urine. This is especially true in the diagnosis of diabetes and kidney disease. The predominant urine protein associated with diabetes is albumin which is the protein most commonly sought out in analyses.

Various methods for determining the presence of protein in urine are known, the most convenient of which involves wetting an absorbant test strip impregnated with a protein error indicator and buffer with a small quantity of urine. Protein error indicators are pH indicators which contain an ionizable group which is displaced in the presence of protein to provide a detectable color change. This is the same color change that the indicator would undergo under the influence of a pH change, so it is important to include buffer in the test strip to thereby avoid a pH increase since such an increase could cause the change of color in the indicator in the absence of protein thereby resulting in a false positive result.

The tendency toward false positive results is particularly problematical with the testing of high SG urine due to the presence in such urine of buffers which overwhelm the buffer in the test strip thereby permitting the change in pH resulting in the color change of the indicator which is indicative of the presence of protein when there is no protein present in the urine sample being tested. The primary buffering component in urine is phosphate, followed by citrate, uric acid, acetate, glycine and ammonium. This sort of false positive is, of course, to be avoided if at all possible. An example of such a false positive situation is a test for urine albumin in which the protein error indicator is Tetrabromophenol Blue, TBPB, which turns from yellow to blue above a pH of 3.7. Another common indicator, DIDNTB, turns from colorless to blue at a pH greater than 2.1. With the use of prior art buffers the addition of high SG urine, which typically has a pH of 5 to 8 and contains buffers which favor the maintenance of high pH thereby increasing the pH of the reagent system to a level of greater than 3.7, causes the color change which results in a false positive reading for protein in the urine sample.

In Japanese Patent Application No. 3-355044 there is described the use of potassium salts to reduce the tendency of false positive responses for protein in high SG urine. While it is stated on page 5 of this application that the mechanism is unclear, this system may operate on the principle that the potassium ion combines with a cation sensing component in urine even though the main components in urine are unresponsive cation sensing buffers. One of the potassium salts mentioned is potassium citrate. This reference also mentions the use of sodium citrate and citric acid as buffers. In example 15 of U.S. Pat. No. 5,279,790 there is described the preparation of a urine protein strip which involves impregnating a paper strip with a mixture of protein error indicators together with a potassium citrate buffer. Citric acid, like most anionic buffers possesses the ability to release some protons in the presence of metallic cations thereby lowering the pH in the presence of such cations. However in order for a cation sensing buffer to benefit the urine protein methodology, the buffer must release enough protons to lower the reagent pH when exposed to cations in the normal physiological ranges found in urine which, even in high SG urine, amount to a maximum of 140 mM for potassium and 250 mM for sodium. Other cations normally found in urine which contribute to this phenomena are calcium, magnesium and ammonium. Citric acid does not possess sufficient proton releasing ability to significantly lower pH at these cation concentrations. The highest urine buffering capacity is 35 meq/pH unit. A protein error indicator test should be resistant to this level of buffering capacity. A high pH (8–9) and a high buffering capacity urine can shift the pH of a citrate buffered reagent by as much as 0.5 units. The combined Na and K cation sensing ability should be greater than 0.5 pH units. The increase of 0.5 in reagent pH due to the buffering capacity of a high SG urine is offset by a decrease of 0.5 in reagent pH due to cation sensing ability of the buffer. The net result is little or no increase in reagent pH due to high SG urine, The combined Na and K cation sensing was 0.71 for tartaric acid and only 0.25 for citrate.

SUMMARY OF THE INVENTION

The present invention involves an improvement to a test strip for the detection of protein in urine which test strip comprises an absorbant carrier impregnated with a reagent system of a buffer and a protein error indicator which undergoes a color change in the presence of protein. The improvement involves the use of a buffer system comprising a typical buffering agent in combination with. tartaric acid as a cation sensing buffer in an amount which renders it capable of releasing sufficient protons in the presence of buffers present in the urine to prevent the pH of the reagent from being elevated to a level at which the protein error indicator will change color in the absence of a significant amount of protein in the urine.

DESCRIPTION OF THE INVENTION

In accordance with the present invention, it has been discovered that test strips for the determination of protein in urine having significantly increased resistance to the buffers normally found in high SG urine can be obtained by preparing an analytical test strip including tartaric acid. More specifically, the present invention provides clinicians with a reliable, simple and accurate method for detecting protein in high SG urine.

One aspect of the present invention is directed to an analytical test strip for the detection of protein in urine which strip comprises an absorbant carrier impregnated with a suitable protein error indicator and a buffer system containing tartaric acid. Suitable protein error indicators include those previously mentioned as well as the merocyanine and nitro or nitroso substituted polyhalogenated phenolsulfonephthaleins disclosed in U.S. Pat. No. 5,279,790 which is incorporated herein by reference. Other suitable protein error indicators include coomassie brilliant blue, Fast Green FCF, Light Green SF, pyrogallol red and pyrocatechol violet. The absorbent carrier of the test strip is preferably a filter paper. Other materials useful as the absorbent carrier include felt, porous ceramic strips and woven or matted glass fibers such as those described in U.S. Pat. No. 3,846,247. Also suitable are wood, cloth, sponge material and argillaceous substances such as those described in U.S. Pat. No. 3,552,928. Alternatively, the absorbent carrier can be of a nonporous material such as a polymeric film or glass. In preparation of the strip, it is impregnated with a solution of the protein error indicator and tartaric acid as buffer. The tartaric acid can be either diprotenated or monoprotenated. The concentration of the error indicator is not critical so long as it provides a strip which contains sufficient error indicator to provide a detectable color change in the presence of protein. The concentration of tartaric acid should be sufficiently high so that, upon contact with the urine it will release sufficient protons in the presence of buffers naturally present in the urine to prevent the pH of the system from being elevated to a level at which the protein error indicator will exhibit a color change in the absence of a significant amount of protein in the urine. Typically, a tartaric acid concentration of 50 to 750 mM (preferably from 500 to 600 mM) in the dip solution will provide a strip containing the requisite concentration after dipping and drying of the absorbent material. The cation sensing ability of tartaric acid renders it more effective than typical buffers, which exhibit their buffering ability by the release of protons when the solution pH is near the pKa of the buffer and equilibrium between the basic and acidic forms of the buffer occurs as in equation 1:

$$HA = H^+ + A^- \qquad (1)$$

Tartaric acid, on the other hand, exerts its buffering activity by sensing cations, i.e. when the release of protons in the presence of cations in solution and equilibrium between the acidic form of the buffer and cation occurs as in equation 2:

$$HA + M^+ = H^+ + AM \qquad (2)$$

This provides a more potent buffering action, so that when tartaric acid is used in combination with one or more typical buffers, it is possible to achieve the necessary buffering capability while using less buffer than would be the case if tartaric acid were not present. Likewise, the concentration of protein error indicator in the solution will typically run from 0.1 to 5.0 mM.

The test strip can also be impregnated with a color enhancing polymer which is typically a polymer having a molecular weight of from about 400 to 25,000 which increases both the kinetics of the color formation and the dose response of the protein error indicators. Preferred color enhancing polymers include polypropylene glycols, polycarbonates, polyvinyl ethers and polyethylene oxides.

While it is preferred that the protein error indicator/tartaric acid be applied to the absorbent carrier and used in the strip format, a wet system in which the urine is contacted directly with the solution may be used. Such a wet system would typically contain the protein error indicator in a concentration of 0.1 to 5.0 mM (preferably 0.6 to 1.0 mM) and the tartaric acid in a concentration of 50 to 750 mM (preferably 500 to 600 mM).

The present invention is further illustrated by the following examples:

Example I (The Relationship of Buffer pKa to Proton Release)

The release of proton upon the addition of cation was demonstrated with oxalic acid. In this experiment the cation was tetramethyl guanidine. This cation is not normally found in urine but was selected since it enhances the response of oxalate and, therefore, more readily allows the relationship of release of proton to cation concentration to be shown. The data are presented in Table 1:

TABLE 1

The pH of Oxalic Acid Solution as a Function of Cation Concentration

| Cation mM | Oxalic Acid mM | Solution pH Initial pH of 0.8 | Solution pH Initial pH of 6 | Molar Ratio of Cation to Oxalic Acid |
|---|---|---|---|---|
| 0 | 50 | 0.80 | 6.22 | 0.0 |
| 10 | 50 | 0.79 | 6.26 | 0.2 |
| 20 | 50 | 0.79 | 6.21 | 0.4 |
| 30 | 50 | 0.74 | 6.21 | 0.6 |
| 40 | 50 | 0.69 | 6.20 | 1.2 |
| 90 | 50 | 0.63 | 6.21 | 1.8 |
| 120 | 50 | 0.61 | 6.26 | 2.4 |
| 150 | 50 | 0.61 | 6.26 | 3.0 |

The pKa of oxalate is 1.27 for the first carboxylic acid group and 4.29 for the second. The release of proton stops once an equivalent number of cations are present for each carboxylic acid group. Alkali and alkaline earth metals and quaternary ammonium salts also produced a release of protons until an equivalent number of cations were present for each carboxylic acid group.

Example II (The Relationship of Buffer to Protein Indicator Dyes)

The protein reagent paper relies on the detection of protein by using the error of a pH indicator in the presence of protein. The principle of this assay is that the pH at which the indicator dye changes color is lower in the presence of protein, causing the color to appear at a fixed pH. The dye is buffered to a constant pH which is low enough to prevent color in the absence of protein, but high enough to create color in the presence of protein. For example, a protein test based on the TBPB dye is buffered to a pH of 3.7 and a test based on the DIDNTB dye is buffered to a pH of 2.1.

In order for a typical buffer to benefit the protein methodology, the buffer must have a pKa in the range of the pH of the protein test. A series of buffers with pKa in the 1.80 to 3.0 range were tested with a protein reagent based on the DIDNTB dye (cf. Table 3). All of the buffers demonstrated buffering capability and maintained the reagent within the 0.7 pH unit after being dipped in a high SG urine. The buffering capacities were dependent upon the individual buffer with the best buffering capacity being demonstrated with tartaric acid while the worst was observed for maleic acid.

TABLE 2

The pH of Reagents After Dipping in Water and High SG Urine as a Function of Buffer

| Buffer | Buffer pK$_1$ | pH of Reagent Dipped in Water | pH of Reagent Dipped in Urine | Reagent pH-Buffer pK$_1$ | Change in Reagent pH |
|---|---|---|---|---|---|
| Citric acid | 3.13 | 2.23 | 2.47 | −0.90 | 0.24 |
| Phosphoric acid | 2.15 | 2.45 | 2.77 | 0.30 | 0.32 |
| Citraconic acid | 2.29 | 2.68 | 2.97 | 0.39 | 0.29 |
| Diglycolic acid | 2.60 | 2.42 | 2.64 | −0.18 | 0.22 |
| Glycylglycine | 3.22 | 2.47 | 2.78 | −0.75 | 0.31 |

TABLE 2-continued

The pH of Reagents After Dipping in Water and High SG Urine as a Function of Buffer

| Buffer | Buffer pK₁ | pH of Reagent Dipped in Water | pH of Reagent Dipped in Urine | Reagent pH-Buffer pK₁ | Change in Reagent pH |
|---|---|---|---|---|---|
| Glycine | 2.34 | 2.44 | 2.72 | 0.10 | 0.28 |
| Maleic acid | 1.91 | 2.39 | 3.00 | 0.48 | 0.61 |
| Malic acid | 3.40 | 2.38 | 2.86 | −1.02 | 0.48 |
| Lysine | 2.18 | 2.40 | 2.87 | 0.22 | 0.47 |
| Tartaric acid | 3.04 | 2.33 | 2.47 | −0.71 | 0.14 |
| Sarcosine | 2.12 | 2.68 | 2.97 | 0.56 | 0.29 |
| Betaine | 1.80 | 2.13 | 2.51 | 0.33 | 0.38 |

Tartaric acid is the buffer of choice in this example because it exhibits the smallest change in pH. This is important because this change is low enough to prevent color formation in the absence of protein. The release of proton upon the addition of cation was only observed in solutions with an initial pH value below or near the pKa of the buffer. The buffer must be partially or fully protonated for there to be a cation response. The concentration of tartrate needed is, of course, dependent upon its degree of protination. A completely deprotonanted buffer would not have any response. Therefore, the relationship between test pH and buffer pKa requires a buffer with a pKa near to or greater than the reagent pH. All of the buffers in Table 3 are at the right conditions, i.e. pKa values of 1.8 to 3.0 which are greater than or near the reagent pH for cation sensing with a pH of 2.1 protein test using DIDNTB dye.

Buffers typically work best when their pKa is near the pH being buffered, i.e. where the buffering capacity is the greatest. However, as can be determined from Table 3, a group of buffers having a similar pKa, within one pH unit of the test pH, have greatly differing effectiveness. Effectiveness is defined as the smallest pH change after contacting the formulation with a high SG urine lacking protein. The pH change with tartrate was only 0.14 whereas the other buffers exhibited pH changes of from 0.22 to 0.61. All of the buffers used have acceptable pKa values for buffering capacity, so the difference is explainable by examining the cation sensing abilities of the buffer. The change in reagent pH represents the combined effects of the buffering capacity and cation sensing action.

The improved buffering capacity of the protein reagent containing tartaric acid is explained by the discovery that solutions of KCl lowered the protein reagent pH (cf. Table 3). The protein reagent containing betaine buffer was not responsive and the citrate buffer was only slightly responsive. Accordingly, it can be seen that betaine and citrate are not cation sensing. There was a 0.63 unit pH decrease with exposure to tartrate while betaine and citrate exhibited virtually no pH decrease due to their failure to act as cation sensing buffers. As shown in Table 2, the differing cation sensing abilities explain variations in buffering capacities between buffers that would be expected to behave in a similar manner.

TABLE 3

The pH of the Protein Reagent After Dipping in a Cation Solution

| Cation | Cation mM | Reagent pH | Reagent Buffer |
|---|---|---|---|
| None | 0 | 2.14 | Tartaric acid |
| KCl | 50 | 1.97 | Tartaric acid |
| KCl | 140 | 1.51 | Tartaric acid |
| MgCl₂ | 10 | 2.15 | Tartaric acid |
| CaCl₂ | 10 | 2.08 | Tartaric acid |
| None | 0 | 3.56 | Citrate |
| KCl | 50 | 3.53 | Citrate |
| KCl | 140 | 3.44 | Citrate |
| MgCl₂ | 10 | 3.50 | Citrate |
| CaCl₂ | 10 | 3.50 | Citrate |
| None | 0 | 2.04 | Betaine |
| KCl | 140 | 2.02 | Betaine |

Most anionic buffers possess some proton release to cations. However, in order for a cation sensing buffer to benefit the urinary protein methodology, the buffer must release enough protons to lower the reagent pH when exposed to cations in the normal physiological ranges. Tartaric acid responded with a 0.6 pH unit decrease when exposed to a concentration of KCl (140 mM) typical for high SG urines. The cation sensing ability of the tartaric acid buffer was further demonstrated by a reagent pH drop of 1.80 after dipping into a high SG clinical urine containing 140 mM potassium and a reagent pH of 2.28 after dipping in a clinical urine containing 41 mM potassium.

The cation sensing agents which are useful in this invention are limited to those with a pKa near to or greater than the reagent pH, which are responsive to cations in urine at the normal physiological range and which provide a decrease in pH capable of offsetting the buffering capacity of urine. Only tartaric acid has been shown to exhibit these properties.

Example III

An experiment was conducted in which tartaric acid (as cation sensing agent) and a typical buffer (citric acid) were tested separately and in combination. The tests were carried out using protein reagent as described in Example 1, with the reagent pH after dipping reagent strips in water and high SG urine determined using a surface PM electrode and pH meter. The difference in pH between water and high SG urine is indicated below as change in reagent pH.

The results of this experiment are set out in Table 4.

TABLE 4

| Citric Acid (Buffer) Concentration | Tartaric Acid (Cation Sensing Agent) Concentration | Change in Reagent pH |
|---|---|---|
| 0 mM | 150 mM | 0.49 |
| 475 mM | 0 mM | 0.37 |
| 475 mM | 150 mM | 0.13 |
| 625 mM | 0 mM | 0.24 |

From Table 4 it can be determined that, the combination of 150 mM tartaric acid as a cation sensing agent with a non-cation sensing buffer such as 475 mM citric acid was more effective than either by itself. It is unexpected that the addition of 150 mM tartaric acid to 475 mM citric acid would produce better SG resistance than 625 mM citric acid. The 150 mM tartaric acid concentration is too low to buffer effectively against a high SG urine such as that used in this experiment. Accordingly, it can be seen that the buffering ability of tartaric acid is not relied upon in controlling pH but instead, the cation sensing activity is the key to tartaric acid's superior performance in controlling pH when combined with a typical buffer.

The ability of tartaric acid in combination with a typical, non-cation sensing buffer in smaller quantities than either agent by itself is important because higher concentrations of any buffer can reduce protein response. A reduced protein response would mean that a pathological protein level would not be detected. This improvement is not limited to citric acid as the non-cation sensing buffer since other buffers, such as, for example, betaine, phosphoric acid, maleic acid, diglycolic acid and citraconic acid, would be expected to provide similar results.

When using tartaric acid in combination with a noncation sensing buffer, the molar ratio of tartaric acid to buffer will typically be from 25 mM:700 mM to 200 mM:100 mM with a ratio of about 150 mM:475 mM being preferred. The cation sensing activity of tartaric acid operates in the absence of a non-cation sensing buffer, however, the use of such a buffer in combination with tartaric acid is preferred because a typical buffer releases protons independent of cations being present in solution. This allows buffering in urines low in salt and brings the reagent's pH closer to the range where the cation sensing tartaric acid can be effective.

Example IV (Procedure for the Preparation of Protein Reagent Example)

The improved protein reagent of the present invention can be made from two sequential saturations of filter paper. The first saturation is with an aqueous mix containing tartaric acid and a buffer such as citric acid, and a background dye such as quinaldine red. The mix is adjusted to pH 2.1 using sodium hydroxide and/or hydrochloric acid. The second saturation involves a toluene mix containing a protein indicator dye such as DIDNTB and a polymer like Lutanol M40 which is a poly (vinyl methyl ether). The function, preferred concentration and range of operable concentrations are set out in Table 5. The mix solutions are used to saturate the strip material, e.g. filter paper such as Ahlstrom 204 or 237 whereupon the filter paper is dried at 95° C. for 5 minutes after the first saturation and at 85° C. for 5 minutes after the second saturation. The resultant dry reagent is processed into reagent strips which were visually tested.

TABLE 5

Protein Reagent Composition

| Ingredient | Function | Pref. Conc. Used | Allowable Range |
|---|---|---|---|
| | | 1st application | |
| Water | Solvent | 1000 mL | — |
| Tartaric acid | Cation Sensing Buffer | 93.8 g (625 mM) | 50–750 mM |
| Quinaldine red | Background dye | 8.6 mg (12 μM) | 5–30 μM |
| | | 2nd application | |
| Toluene | Solvent | 1000 mL | — |
| DIDNTB | Buffer | 0.61 g (0.6 mM) | 0.1–3.0 mM |
| Lutonal M40 | Polymer enhancer | 1.0 g | 0.5–4 g/L |

DIDNTB = 5',5"-Dinitro-3',3"-Diiodo-3,4,5,6-Tetrabromophenolsulfonephthalein

Example V (Relationship of Buffer to the Background Dye)

Reagent formulations often employ background dyes to achieve better visual distinction between test levels. For example, a protein test based on DIDNTB as the dye indicator, which undergoes a colorless to blue transition, requires a red background dye to change the color transition from pink to blue in order to mask detection of normal levels of protein to reduce the sensitivity of the test since a faint blue is easily detected against white but not under a red background. The background dye should be inert to urine components and provide a constant response. The differences between an inert and background dye can be demonstrated by comparing inert methyl red to reactive quinaldine red as set out in Table 6.

Quinaldine red is both pH and light sensitive; its color transition is from colorless at pH 1.4 and, with increasing pH up to 3.4, forms various shades of red with maximum absorbance at pH 3.4. The quinaldine red pKa of 2.1 is at the pH of a protein test based on the DIDNTB dye.

TABLE 6

| | | | | CLINITEK-200 | Reactivity |
|---|---|---|---|---|---|
| Background Dye | pH | λ max | light | Negative | Positive |
| Quinaldine Red | 1.7 | 528 nm | Unexposed | 1006 | 694 |
| Quinaldine Red | 2.1 | 528 nm | Unexposed | 1005 | 525 |
| Quinaldine Red | 2.1 | 528 nm | Exposed | 953 | 497 |

The positive level as 30 mg/dL albumin. Light exposure to 105 ft-candles for 15 minutes.

Methyl red is neither pH nor light sensitive. No change in reactivity was observed after exposure to lighting conditions affecting the quinaldine red dye. The methyl red color transition is from red at pH 4.2 to yellow at pH 6.4. The methyl red, pKa 5.2, prevented changes in background coloration due to pH and, therefore, is a preferred dye. Other inert dyes such as FD&C red #3 and Acid Red #40 can also be used.

Example VI

The cation sensing abilities of the buffers listed in Table 2 were measured and are set out in Table 7 below:

TABLE 7

| | pH Changes After Adding | |
|---|---|---|
| Buffer | KCl | NaCl |
| Tartaric Acid | −0.50 | −0.21 |
| Citric Acid | −0.07 | −0.16 |
| Glycine | −0.03 | 0.03 |
| Phosphoric Acid | −0.08 | −0.12 |
| Maleic Acid | −0.05 | −0.13 |
| Malic Acid | −0.06 | −0.14 |
| Lysine | 0.00 | −0.02 |
| Betaine | 0.00 | −0.05 |

This experiment measured the change in pH of a 500 mM buffer solution after adding 140 mM KCl or 250 mM NaCl. These salt concentrations were taken as the highest urinary values, i.e. the highest physiological concentration expected in human urine. The data of Table 7 demonstrate that tartaric acid is the most responsive to cations of the buffers tested. The data in Table 3 were generated using dry reagents made and tested in a similar fashion. The other buffers tested are not useful for cation sensing. Oxalate demonstrates a cation response (Table 1), but this response is not great enough for use in the present invention.

What is claimed is:

1. In a test strip for the detection of protein in urine which comprises an absorbant carrier impregnated with a reagent system of a buffer and a protein error indicator which undergoes a color change in the presence of protein, the improvement which comprises the use of tartaric acid as a cation sensing agent in the reagent system in combination with a non-cation sensing buffer as the buffer in an amount capable of preventing the pH of the reagent system from being elevated to a level at which the protein error indicator will change color in the absence of a significant amount of protein in urine wherein the amount of tartaric acid is the residue left in the absorbant carrier after dipping it into a solution comprising both tartaric acid and the non-cation sensing buffer having a tartaric acid concentration of 50 to 750 mM and the amount of non-cation sensing buffer is the residue left in the absorbant carrier after dipping it into the same solution in which the ratio of tartaric acid to non-cation sensing buffer is from 25 mM:700 mM to 200 mM:100 mM.

2. The strip of claim 1 wherein the tartaric acid and non-cation sensing buffer are present in sufficient concentration to lower the pH of the reagent system by at least about 0.5 pH units when the reagent system is contacted with urine containing potassium ion at a concentration of 140 mM.

3. The strip of claim 1 wherein the protein error indicator is Tetrabromophenol Blue or 5',5,"-Dinitro-3,3"-Diiodo-3,4,5,6-Tetrabromophenolsulfonephthalein.

4. The strip of claim 1 wherein the absorbant carrier is filter paper.

5. The strip of claim 1 wherein the amount of protein error indicator in the reagent system is the residue left in the absorbant carrier after dipping the absorbant carrier into a solution of indicator having an indicator concentration of 0.1 to 5.0 mM.

6. The strip of claim 1 wherein the tartaric acid concentration is from 500 to 600 mM.

7. The strip of claim 6 wherein the ratio is about 150 mM:475 mM.

8. The strip of claim 1 wherein the tartaric acid is diprotonated.

9. The strip of claim 1 wherein the tartaric acid is monoprotonated.

10. The strip of claim 1 wherein there is included within the reagent system a background dye.

11. The strip of claim 10 wherein the background dye is selected from those dyes which are not sensitive to pH or light.

12. The strip of claim 10 wherein the background dye is methyl red, FD&C red #3 or Acid Red #40.

13. A test for protein in urine which comprises the steps of:
a) contacting a urine sample with a test strip of an absorbant material having absorbed therein a buffer system and a protein error indicator wherein the buffer system comprises tartaric acid and a non-cation sensing buffer with the amount of tartaric acid in the strip being the residue left therein after dipping the absorbant material into a solution comprising both tartaric acid and the non-cation sensing buffer having a tartaric acid concentration of 50 to 750 mM and the amount of non-cation sensing buffer being the residue left in the absorbant material after dipping it into the same solution in which the ratio of tartaric acid to non-cation sensing buffer is from 25 mM:700 mM to 200 mM:100 mM to cause a change in the color of the protein error indicator when protein is present in the urine; and
b) correlating the change in color of the protein error indicator with the concentration of protein in the urine sample being tested.

* * * * *